US011839668B2

United States Patent
Douezan et al.

(10) Patent No.: US 11,839,668 B2
(45) Date of Patent: *Dec. 12, 2023

(54) COMPOSITION COMPRISING PHOTONIC PARTICLES, A UV-SCREENING AGENT AND AN ACRYLIC POLYMER

(71) Applicant: L'OREAL, Paris (FR)

(72) Inventors: Stéphane Douezan, Chevilly la Rue (FR); Angélina Roudot, Chevilly la Rue (FR)

(73) Assignee: L'OREAL, Paris (FR)

( * ) Notice: Subject to any disclaimer, the term of this patent is extended or adjusted under 35 U.S.C. 154(b) by 74 days.

This patent is subject to a terminal disclaimer.

(21) Appl. No.: 16/763,431

(22) PCT Filed: Nov. 15, 2018

(86) PCT No.: PCT/EP2018/081474
§ 371 (c)(1),
(2) Date: May 12, 2020

(87) PCT Pub. No.: WO2019/096959
PCT Pub. Date: May 23, 2019

(65) Prior Publication Data
US 2020/0330334 A1 Oct. 22, 2020

(30) Foreign Application Priority Data
Nov. 15, 2017 (FR) ....................................... 1760731

(51) Int. Cl.
| | | |
|---|---|---|
| *A61K 8/02* | (2006.01) | |
| *A61K 8/25* | (2006.01) | |
| *A61K 8/37* | (2006.01) | |
| *A61K 8/81* | (2006.01) | |
| *A61Q 17/04* | (2006.01) | |
| *A61Q 19/08* | (2006.01) | |
| *C08F 220/68* | (2006.01) | |
| *C08F 220/06* | (2006.01) | |

(52) U.S. Cl.
CPC ............... *A61K 8/025* (2013.01); *A61K 8/25* (2013.01); *A61K 8/37* (2013.01); *A61K 8/8152* (2013.01); *A61Q 17/04* (2013.01); *A61Q 19/08* (2013.01); *C08F 220/06* (2013.01); *A61K 2800/26* (2013.01); *A61K 2800/412* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 4,128,635 A | 12/1978 | Hase et al. | |
| 2004/0005279 A1 | 1/2004 | Lorant et al. | |
| 2007/0264204 A1* | 11/2007 | Noor .................... | A61K 8/585 424/47 |
| 2009/0105353 A1 | 4/2009 | Lorant | |
| 2010/0202985 A1 | 8/2010 | Sen Gupta | |
| 2011/0097288 A1 | 4/2011 | Janssen | |
| 2012/0244202 A1* | 9/2012 | Simonnet ............... | A61Q 17/04 977/773 |
| 2013/0052148 A1 | 2/2013 | Chavan | |
| 2017/0348219 A1 | 12/2017 | Uyama | |

FOREIGN PATENT DOCUMENTS

| | | |
|---|---|---|
| DE | 26 08 875 A1 | 9/1977 |
| EP | 1 386 600 A1 | 2/2004 |
| EP | 2 039 339 A2 | 3/2009 |
| EP | 3 235 839 A1 | 10/2017 |
| FR | 2 843 020 A1 | 2/2004 |
| FR | 3 046 076 A1 | 6/2017 |
| GB | 1 560 428 A | 2/1980 |
| JP | 52 108030 A | 9/1977 |
| JP | 2009 120493 A | 6/2009 |
| JP | 2009 536949 A | 10/2009 |
| JP | 2012 144580 A | 8/2012 |
| JP | 2013 520464 A | 6/2013 |
| JP | 2014 185137 A | 10/2014 |
| JP | 2015 131767 A | 7/2015 |
| JP | 2015 164970 A | 9/2015 |
| WO | WO 2007 133720 A2 | 11/2007 |
| WO | WO 2011 104228 A1 | 9/2011 |
| WO | WO 2016 098456 A1 | 6/2016 |

OTHER PUBLICATIONS

Epstein, H. "Skin Care Products." in Handbook of Cosmetic Science and Technology, 3rd Edition (2009) 121-134. (Year: 2009).*
JPO English abstract for JP 2015-131767 (Sase et al.) (Year: 2015).
Derwent English abstract for JP 2012-144580 (Sekiguchi et al.) (Year: 2012).
Machine-assisted English translation for JP 2015-131767 (Sase et al.) (Year: 2015).
Machine-assisted English translation for JP 2012-144580 (Sekiguchi et al.) (Year: 2012).

* cited by examiner

*Primary Examiner* — Bethany P Barham
*Assistant Examiner* — Peter Anthopolos
(74) *Attorney, Agent, or Firm* — POLSINELLI PC

(57) ABSTRACT

The present invention relates to a composition, especially a photoprotective cosmetic composition, comprising at least: photonic particles having a mean size of from 0.5 μm to 100 μm, each including an ordered periodic arrangement of monodisperse nanoparticles or of empty spaces, leading to attenuation of the radiation in the wavelength range extending from 250 nm to 1800 nm, preferably from 250 nm to 400 nm, b) at least one UV-screening agent, and at least one particular acrylic polymer.

22 Claims, No Drawings

COMPOSITION COMPRISING PHOTONIC PARTICLES, A UV-SCREENING AGENT AND AN ACRYLIC POLYMER

CROSS REFERENCE TO RELATED APPLICATIONS

This application is a National Phase filing under 35 U.S.C. § 371 of PCT/EP2018/081474 filed on 15 Nov. 2018; which application in turn claims priority to Application No. 1760731 filed in France on 15 Nov. 2017. The entire contents of each application are hereby incorporated by reference.

The invention relates to a composition, especially a cosmetic composition and in particular a photoprotective composition, and to a process for treating keratin materials, in particular the skin and its integuments, using said composition.

It is known that light radiation with wavelengths of between 280 and 400 nm makes it possible to brown the human epidermis. However, rays with wavelengths more particularly between 280 and 320 nm, known as UVB rays, cause skin erythema and burns which can be detrimental to the development of a natural tan.

For these reasons, and also for aesthetic reasons, there is constant demand for means for controlling this natural tanning in order to control the colour of the skin; this UVB radiation should thus be screened out.

It is also known that UVA rays, with wavelengths of between 320 and 400 nm, and which cause tanning of the skin, are liable to induce adverse changes therein, in particular in the case of sensitive skin or skin that is continually exposed to solar radiation. UVA rays cause in particular a loss in the elasticity of the skin and the appearance of wrinkles, resulting in premature skin ageing.

It is therefore desirable also to screen out UVA radiation.

Many photoprotective compositions have been proposed to date for protecting against the effects induced by UVA and/or UVB radiation. These compositions generally contain organic or mineral screening agents, more particularly mixtures of organic liposoluble screening agents and/or of water-soluble screening agents, combined with metal oxide pigments such as titanium dioxide or zinc oxide. These inorganic particles make it possible to increase the sun protection, which reduces the amount of organic screening agents and can thus improve the cosmeticity of the formulations.

While mineral screening agents such as titanium dioxide or zinc oxide are widely used in cosmetics for their UV-Absorbing properties, they cause, however, whitening when they are applied to the skin, which is not attractive.

It is known practice from patent application WO 06/136724 to use monodisperse particles that are capable of forming a network and that have optical properties of filtering in the UVB, UVA and infra-red ranges. In said patent application, the particles must be organized on the skin.

This type of material has especially been used in two-phase cosmetic compositions, comprising a continuous aqueous phase in which are dispersed solid photonic particles.

This type of composition affords access to a high SPF, but a drawback thereof is the sedimentation and aggregation of the photonic particles, which form a block that is very difficult to redisperse once formed. This drawback harms the performance of the composition in the long term since the amount of photonic particles really dispersed has a tendency to decrease over time.

The materials (or photonic particles), and in particular opals, are colloidal crystals, i.e. three-dimensional periodic structures based on the assembly of colloidal particles or of empty spaces. These assemblies enable physical attenuation of UV rays. This attenuation is adjusted by the periodicity of the lattice in the material and its refractive index, in particular the difference in index between the material and the medium.

It is advantageous to convey photonic particles in an aqueous phase in order to ensure a maximum difference in index between the material and the medium. Photonic materials are difficult to formulate as emulsions since they have a tendency to migrate into the fatty phase or to position themselves at the interface of the emulsion droplets. Their efficacy is then reduced. High-SPF compositions in the form of emulsions in which the photoprotective properties of the photonic materials are expressed without compromising the cosmetic properties such as the greasy, tacky and/or white finish are sought.

The inventors have found, surprisingly, that the addition of a particular acrylic polymer makes it possible to obtain stable, high-SPF emulsions with improved cosmetic properties. In particular, after application to the skin, there is no whitening effect, the skin is soft and is neither greasy nor tacky.

According to a first of its aspects, the invention relates to a composition, especially a cosmetic composition, in particular a photoprotective composition, comprising at least:
a) photonic particles having a mean size of from 0.5 µm to 100 µm, each including an ordered periodic arrangement of monodisperse nanoparticles or of empty spaces, leading to attenuation of the radiation in the wavelength range extending from 250 nm to 1800 nm, preferably from 250 nm to 400 nm, and
b) at least one UV-screening agent, and
c) at least one polymer described below.

According to another of its aspects, the invention relates to a process for preparing the composition according to the invention, including a step of dispersing, in a cosmetically acceptable medium, photonic particles according to the invention and a polymer c) as defined above.

According to another of its aspects, the invention relates to a cosmetic and especially photoprotective composition comprising, in a physiologically acceptable medium, a composition according to the invention as defined above.

The cosmetic and especially photoprotective composition according to the invention is particularly suitable for use in a non-therapeutic process for the photoprotection of keratin materials.

The photoprotective cosmetic composition according to the invention has, for example, an SPF of at least 5, or even of at least 10, better still 15, better still at least 30, 45 or 60. The SPF (sunscreen protection factor) is defined in the article *A new substrate to measure sunscreen protection factors throughout the ultraviolet spectrum*, J. Soc. Cosmet. Chem., 40, 127-133 (May/June 1989).

The formulation of the photoprotective cosmetic composition is chosen, for example, such that the composition has a transmission factor of less than or equal to 70%, 60%, 50%, 40%, 30%, 20%, 10%, 5% or better still 1%, for at least one wavelength in the range 250-400 nm, better still for the entirety of this range. The screening is proportionately better the lower the transmission factor in the range 250-400 nm.

According to another of its aspects, the invention relates to a non-therapeutic process for the photoprotection of keratin materials with respect to solar UV radiation, comprising a step of applying a cosmetic composition according to the invention to said keratin materials.

The invention also relates to a process for dyeing and/or lightening keratin materials, and to a process for modifying the spectral reflectance of keratin materials, each of these processes comprising a step of applying a cosmetic composition according to the invention to said keratin materials.

The invention also relates to a non-therapeutic cosmetic process for limiting the darkening of the skin and/or improving the colour and/or uniformity of the complexion, comprising a step of applying a cosmetic composition according to the invention to the skin.

The invention also relates to a non-therapeutic cosmetic process for preventing and/or treating the signs of ageing of a keratin material, comprising a step of applying a cosmetic composition according to the invention to the surface of said keratin material.

In the text hereinbelow, and unless otherwise indicated, the limits of a range of values are included within that range, especially in the expressions "between" and "ranging from . . . to . . . ".

Moreover, the expressions "one or more" and "greater than or equal to" used in the present description are equivalent to the expressions "at least one" and "at least", respectively.

Photonic Particles

In the context of the invention, the photonic particles are also called opals.

Preferably, the photonic particles are present in the composition in the form of a dispersion.

The photonic particles may have a form factor of less than 2, especially less than 1.75. The form factor denotes, when the particle is oblong, the ratio of its greatest longitudinal dimension to its greatest transverse dimension. The photonic particles may be substantially spherical, then having a form factor equal to 1.

A form factor of less than 2 may be advantageous in terms of surface coverage, relative to flat particles that can superimpose.

The mean size of the photonic particles is from 0.5 µm to 100 µm, preferably from 1 µm to 40 µm, advantageously from 5 µm to 25 µm, preferentially from 5 µm to 20 µm or even from 5 µm to 15 µm.

The term "mean size" denotes the statistical particle size dimension for half the population, referred to as D (0.5).

The photonic particles according to the invention may include filled or hollow nanoparticles ordered without a matrix or ordered or dispersed within any type of matrix, for example dispersed in a heat-, electro- or photo-crosslinkable matrix.

Photonic particles according to the invention may be, depending on the variants, qualified as direct, inverse or pseudo-inverse opals, as described below.

The photonic particles may be colourless.
The photonic particles may be filled or hollow.
Direct Opals The photonic particles of "direct opal" type involve an arrangement of optionally composite, filled nanoparticles.

The photonic particles may include aggregated nanoparticles, preferably without a matrix.

A first process for manufacturing such particles, may, as described in the publication by S-H Kim et al., JACS, 2006, 128, 10897-10904, include a step of obtaining a water-in-oil emulsion, the aqueous phase including monodisperse nanoparticles, followed by a step of obtaining photonic particles including a step of microwave irradiation of the emulsion obtained previously.

A second manufacturing process may, as described in the publication by S-M. Yang, Langmuir 2005, 21, 10416-10421, include a step of aggregating $SiO_2$ or polystyrene nanoparticles under an electrospray.

Photonic particles of "direct opal" type may also be obtained via a process as described in the publication "Ordered macroporous titania photonic balls by micrometer-scale spherical assembly templating" by Li et al., J. Mater. Chem., 2005, 15, 2551-2556.

Photonic particles of "direct opal" type may also be obtained via an atomization process.

According to this process, the particles to be atomized are first dispersed in a water-based medium or in a homogeneous water/solvent mixture, said solvent being water-miscible, for instance an alcohol such as ethanol. The particle concentration may be from 5% to 70% by weight. The dispersion thus obtained is introduced into an atomizer, for instance Niro Minor Production; the injection rate (in the case of this machine) may be between 1000 and 10 000 g/h and preferably between 2000 and 8000 g/h. The turbine speed is very high, preferably between 25 000 and 45 000 rpm. The atomization temperature may be between 100 and 500° C. and preferably between 200 and 350° C.

The photonic particles of "direct opal" type may also include nanoparticles aggregated in a matrix, in contact with each other, or dispersed in a matrix.

Several processes, in addition to the processes described previously, may be suitable for manufacturing these photonic particles, especially the process of aggregation of $SiO_2$ particles in a silicon matrix, described in patent application US 2003/0148088.

A second process may, as described in the publication by D. Pine, Langmuir 2005, 21, 6669-6674, include a step of aggregation using an emulsion of PMMA nanoparticles.

The photonic particles of "direct opal" type may include nanoparticles dispersed in a photo-, electro- or heat-crosslinkable organic matrix.

The advantage of using a photo-crosslinkable, electro-crosslinkable or heat-crosslinkable organic matrix, especially a photo-crosslinkable or heat-crosslinkable matrix, lies in the possibility of modifying the distance between the nanoparticles contained in the matrix so as to vary the optical properties of the photonic particle. This distance may depend on the weight fraction of nanoparticles dispersed in the organic matrix, before photo-, electro- or heat-crosslinking, especially before photo- or heat-crosslinking. Said weight fraction is equal to the ratio of the weight of nanoparticles/weight of the matrix before heat-, electro- or photo-crosslinking.

According to a preferred embodiment of the invention, this weight fraction of nanoparticles is between 1% and 90% and better still between 5% and 60%.

This type of photonic particle may be obtained according to several emulsification processes, for example those described in the publication by S-H Kim et al., Adv. Mater. 2008, 9999, 1-7 which uses silica particles dispersed in a UV-photopolymerizable ETPTA (ethoxylated trimethylolpropane triacrylate) photo-crosslinkable resin or in the publication "Ordered macroporous titania photonic balls by micrometer-scale spherical assembly templating" by Li et al., J. Mater. Chem., 2005, 15, 2551-2556.

In certain examples, the photonic particles are constituted of aggregated silica nanoparticles, without a matrix.

Inverse Opals

The photonic particles of "inverse opal" type include holes instead of nanoparticles.

They may be obtained from direct opals after destruction, for example by calcination or acidic hydrolysis, for example with 5% hydrofluoric acid, of the nanoparticles, thus leaving empty spaces in place of all or some of the nanoparticles. The destruction step may possibly bring about a reduction in the size of the nanoparticle's imprint in the matrix, which may be up to 50%.

The calcination (500° C. to 1000° C.) may be performed on direct opals based on organic nanoparticles and an inorganic matrix.

The acidic hydrolysis, for example with a hydrofluoric acid solution, may be performed on opals based on inorganic nanoparticles and an organic matrix.

In the case of inverse opals, the ratio of the volume occupied by the nanoparticles/volume occupied by the matrix (organic or precursor of the inorganic matrix) may be varied from 99/1 to 80/20, which will have the effect of varying the surface porosity of the inverse opals. Such a variation is presented in the publication by D. Pine and F. Lange, Langmuir 2005, 21, 6669-6674.

The inverse opals may be produced via the processes already described above for the direct opals including nanoparticles aggregated or dispersed in a matrix, followed by a step of destroying the nanoparticles, for example by calcination or acidic hydrolysis, for example as described in the following publications:

A. Stein: Chem. Mater. 2002, 14, 3305-3315 in which the opals are made from monodisperse particles in zirconium acetate matrices for the ZrO objects, in titanium propoxide matrices for the $TiO_2$ opals, or in tetramethoxysilane (TMOS) matrices for the silica opals. After calcination, the PS particles leave empty spaces. The final material is then ground to give opal powder.

D. Pine, F. F. Lange: Langmuir, Vol. 21, 15, 2005, 6669-6674 which describes the production of opals in the form of spheres via an emulsification process followed by a step of calcination of the PMMA particles. The opal porosity is controlled by the titanium alkoxide/PMMA particle content ratio.

F. F. Lange, Colloid Polym. Sci. (2003) 282, 7-13 which describes the emulsification of PMMA particles in the presence of titanium butoxide followed by calcination of the PMMA particles.

By nature, inverse opals have no additional treatment of the porous materials whose optical properties will vary as a function of the medium, that may fill the holes in the opals.

In order to ensure the optical properties irrespective of the medium, photonic particles of inverse opal structure may be coated and rendered leaktight with respect to the medium in which they are immersed.

This coating may be done, for example, with polymers or waxes.

Several processes are possible:

spray-drying or atomization: the principle is to solubilize or disperse (for lattices) the material that will coat the photonic particles in a volatile solvent with an evaporation point less than or equal to 100° C. (ethanol, acetone, isopropanol, water, etc. or mixtures thereof). The whole is sprayed in a chamber brought to a temperature that allows the solvent or mixture to evaporate, leading to deposition of the coating material on the particles. Said particles are entrained, under the effect of a stream of air, into a container at room temperature, and are collected therein. For example, mention may be made of the publication "Effects of fabrication conditions on the characteristics of etamidazole spray dried microspheres": Wang et al., J. Microencapsulation, 2002, vol. 19, No. 4, 495-510.

fluidized air bed: the fluidized air bed process is a method used frequently for drying and making granules. A stream of warm air is introduced via the base of the reactor. The suspension sprayed by an atomizer into the production chamber makes the particles in suspension grow, and they fall to the ground as soon they can no longer be borne by the air stream.

In a non-limiting manner, the materials for coating the particles may be chosen from:

waxes and fatty substances with a melting point above 45° C., especially carnauba wax, beeswax, stearyl stearate, polyethylene wax, DI 18/22 adipate, pentaerythrityl tetrastearate, tetracontanyl stearate or dioctadecyl carbonate, cellulose and cellulose derivatives, especially ethylcellulose, hydroxypropylcellulose, hydroxypropylmethylcellulose, hydroxybutylcellulose, and the polymers sold under the brand name Ethocel®, polycaprolactone with a molecular weight from 10 000 to 80 000 g/mol, polylactic acid (PLA) and polylactic acid-glycolic acid (PLAGA) in a 90/10 to 50/50 ratio, polyvinyl alcohol, copolymers of polyvinylpyrrolidone and of vinyl acetate, and copolymers of acrylic acid and of methyl methacrylate sold under the brand name Eudragit® L100.

The mass ratio between the core of the photonic particle and the shell thus made may be between 99.9/0.1 and 80/20, and preferably between 99/1 and 90/10.

Pseudo-Inverse Opals

The photonic particles of "pseudo-inverse opal" type include hollow nanoparticles aggregated without a matrix or aggregated or dispersed within any type of matrix, for example dispersed in a heat-, electro- or photo-crosslinkable matrix.

Making direct opals from hollow nanoparticles, also called "pseudo-inverse opals", has the advantages of amplifying the optical effects by a higher index difference compared with direct opals that do not use hollow nanoparticles, and of offering zero porosity compared with uncoated inverse opals, whose optical properties are dependent on the medium in which they are dispersed.

The hollow nanoparticles may be as described below.

Janus-Type Photonic Particles

The photonic particles may be of Janus type, i.e. they may include at least one other diffracting arrangement of nanoparticles, or even at least two other diffracting arrangements, the arrangements each having intrinsic optical properties, especially different diffraction spectra.

In a first embodiment, one arrangement may include filled nanoparticles and another arrangement may include filled or hollow nanoparticles.

As a variant, one arrangement may include hollow nanoparticles and another arrangement may include hollow nanoparticles.

When the particles include several arrangements, each arrangement may cover, for example, a portion of the UV spectrum, so as to obtain broadened photoprotection.

The photonic particles including several diffracting arrangements may be obtained as taught in the publication by S-H. Kim et al., Adv. Mater. 2008, 9999, 1-7 or the publication "Patterned colloidal photonic domes and balls derived from viscous photocurable suspensions" by Kim et al., Adv. Mater. 2008, 20, 3211-3217.

When the photonic particles are used at least in part for their colour properties, particularly for homogenization of the complexion, the arrangements of nanoparticles, when lit by white light, may produce different respective colours; the arrangements may especially produce red, green and/or blue, thereby allowing the production of a large number of tones and particularly white by additive synthesis of reflected light.

An arrangement has a red reflected colour, for example, when the reflectance in the visible spectrum is at least 50% in the wavelength range extending from 620 to 700 nm, for an observation angle varying between 30 and 150°. For green, the wavelength range under consideration extends from 490 to 550 nm and for blue from 410 to 490 nm. The arrangements may diffract light through different respective zones of the photonic particle, for example two opposite zones, for example two diametrically opposite hemispherical zones in the case of a spherical photonic particle.

One of the arrangements may have a diffraction spectrum with at least one first-order reflection peak in the wavelength range from 250 to 400 nm and another arrangement may have a diffraction spectrum with at least one first-order reflection peak in the wavelength range from 250 to 400 nm or 400 to 700 nm.

Mixture of Photonic Particles

The composition according to the invention may include photonic particles of only one type or a mixture of at least two different types of photonic particles, for example having reflection peaks, especially of first order, centred on different wavelengths, located in the visible, UV or near-IR region.

The composition may, for example, include a mixture of one type of photonic particles including filled nanoparticles and another type of photonic particles including nanoparticles that may be filled or hollow.

The composition may, for example, include a mixture of one type of photonic particles including hollow nanoparticles and another type of photonic particles including nanoparticles that may be hollow.

The composition may, for example, include a mixture of one type of photonic particles including a heat-, electro- or photo-crosslinkable matrix and another type of photonic particles not including a heat-, electro- or photo-crosslinkable matrix.

Nanoparticles

The nanoparticles constituting the photonic particles may have a mean size of from 100 nm to 500 nm and preferably from 100 nm to 400 nm.

The term "mean size" denotes the statistical particle size dimension for half the population, referred to as D (0.5).

The nanoparticles may be of spherical shape.

The nanoparticles may be monodisperse to 15% or better. The term "monodisperse to x %" refers according to the invention to particles whose mean size has a coefficient of variation CV of less than or equal to x %.

The coefficient of variation CV is defined by the relationship:

$CV=s/D$, s being the standard deviation of the particle size distribution, and

D being the mean size of said particles.

The mean size D and the standard deviation s may be measured on 250 particles by analysis of an image obtained using a scanning electron microscope, for example the machine referenced S-4 500 from the company Hitachi. Image analysis software may be used to facilitate this measurement, for example the Winroof® software sold by the company Mitani Corporation. Preferably, the coefficient of variation of the monodisperse nanoparticles is less than or equal to 10%, better still less than or equal to 7%, or even better still less than or equal to 5%, for example being substantially of the order of 3.5% or less.

The nanoparticles may be filled or hollow, and organic or inorganic.

The nanoparticles may be monomaterial or composite.

When the monodisperse nanoparticles are composite, they may, for example, include a core and a shell made of different materials, for example organic and/or mineral materials.

Inorganic Nanoparticles

The nanoparticles may include an inorganic compound, or even may be entirely mineral.

When the nanoparticles are inorganic, they may include, for example, at least one oxide, especially a metal oxide, for example chosen from silica, silicon, iron, titanium, aluminium, chromium, zinc, copper, zirconium and cerium oxides, and mixtures thereof. The nanoparticles may also include a metal, especially titanium, silver, gold, aluminium, zinc, iron or copper and mixtures and alloys thereof.

According to one embodiment, the nanoparticles comprise silica, at least one metal oxide, especially as described above, or a mixture of silica and of at least one metal oxide, especially as described above.

Organic Nanoparticles

The nanoparticles may include an organic compound, or even may be entirely organic.

Among the materials that may be suitable for making organic nanoparticles, mention may be made of polymers, especially with carbon-based or silicon-based chains, for example polystyrene (PS), polymethyl methacrylate (PMMA), polyacrylamide (PAM), silicone polymers, NADs ("non-aqueous dispersions"), for instance rigid NADs that, as examples, are constituted of 96.7% methyl methacrylate and 3.3% ethylene glycol dimethacrylate crosslinked at 20% in isododecane, particle diameter: 141 nm (polydispersity Q=0.14) or 90% methyl methacrylate and 10% allyl methacrylate, particle diameter: 170 nm or 100% methyl dimethacrylate, particle diameter: 138 nm (polydispersity Q=0.15) or poly(methyl methacrylate/allyl methacrylate, polylactic acid (PLA), polylactic acid-glycolic acid (PLAGA), celluloses and derivatives thereof, polyurethane, polycaprolactone, latex form, chitin, composite chitin materials.

The glass transition temperature ($T_g$) of the organic nanoparticles may be greater than 40° C. and better still greater than 60° C.

Hollow Nanoparticles

These nanoparticles include a core and a shell. The core may be organic or inorganic.

The nanoparticle shell may, for example, be made of PS and the particles may, for example, be aggregated within an organic matrix.

The nanoparticle shell may, for example, be made of PS and the particles may, for example, be dispersed within an organic heat-, electro- or photo-crosslinkable matrix.

The core of these hollow nanoparticles may be constituted by air or a gas other than air so as to benefit from a different refractive index, for example $CO_2$, $N_2$, butane or isobutane.

The presence of air or another gas inside the hollow nanoparticles may make it possible to obtain a great difference in refractive index between the nanoparticles and the surrounding medium, which is favourable in terms of intensity of the diffraction peak.

When the nanoparticles are hollow, the difference in refractive index at a diffracted wavelength between the core and the shell may be greater than or equal to 0.4. Said diffracted wavelength may be between 250 and 800 nm, for example between 250 and 400 nm. When the nanoparticles are hollow, the ratio between a largest dimension of the core and a largest dimension of the nanoparticle may be between 0.5 and 0.8. When the nanoparticles are hollow, the core volume represents between 10% and 80% and preferably between 20% and 60% of the total volume of the nanoparticle.

The thickness of the shell of the hollow nanoparticles, taken as equal to half the difference of the largest dimension of the nanoparticle and the largest dimension of the core of the nanoparticle, may be between 50 and 200 nm, for example between 30 and 100 nm.

Among the hollow nanoparticles that may be used, mention may be made of the 280 nm nanoparticles SX866(B) from the company JSR.

The core of the nanoparticles may optionally comprise a sunscreen or a mixture of sunscreens.

Matrix

The photonic particles may include filled or hollow nanoparticles, which are aggregated or dispersed in any type of matrix, for example dispersed in a heat-, electro- or photo-crosslinkable matrix, or empty spaces dispersed in any type of matrix, for example dispersed in a heat-, electro- or photo-crosslinkable matrix, as mentioned above.

The matrix may be organic or inorganic.

Among the organic matrices, mention may be made, in a non-limiting manner, of acrylic matrices: made of polymethyl methacrylate (PMMA) or polyacrylamide (PAM), matrices made of polyethylene terephthalate (PET), polystyrene (PS), polycaprolactone (PCL), polyvinyl acetate (PVA), polyvinylethyl acetate (PVEA), waxes with a melting point above 65° C., for example above 75° C., and with a hardness above 5 MPa and preferably above 6 MPa.

In particular, the matrix may be heat-crosslinkable, photo-crosslinkable or electro-crosslinkable.

The term "photo-crosslinkable matrix" should be understood as meaning a matrix whose crosslinking is induced and/or assisted by light radiation, especially UV.

The term "heat-crosslinkable matrix" should be understood as meaning a matrix whose crosslinking is induced and/or assisted by a supply of heat, for example bringing the matrix to a temperature above 60° C.

The term "electro-crosslinkable matrix" should be understood as meaning a matrix whose crosslinking is induced and/or assisted by applying an electric field.

A matrix may be both heat-crosslinkable and photo-crosslinkable.

The photonic particles may include filled or hollow nanoparticles, dispersed in a heat-, electro- or photo-crosslinkable matrix or empty spaces dispersed in a heat-, electro- or photo-crosslinkable matrix.

The heat-crosslinkable or photo-crosslinkable matrix may be organic.

Among the crosslinkable organic matrices, mention may be made in a non-limiting manner of:

photo-crosslinkable polymers, such as ETPA (Ethoxylated TrimethylolPropane triAcrylate), PEGDA (polyethylene glycol diacrylate), acrylic resins, PEG diacrylates, and the materials described in FR 2 833 487, copolymers, described in FR 2 848 428 which crosslink by polycycloaddition, of PVA or of PVEA and of styrylpyridiniums having the following formula:

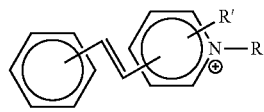

in which R represents a hydrogen atom, an alkyl or hydroxyalkyl group, and R' represents a hydrogen atom or an alkyl group, the reactive silicones described in patent FR 2 910 286, i.e.: polyorganosiloxanes including siloxane units of formula:

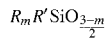

in which R is a linear or cyclic monovalent hydrocarbon-based group, including from 1 to 30 carbon atoms, m is equal to 1 or 2 and R' is an unsaturated aliphatic hydrocarbon-based group including from 2 to 10 carbon atoms or an unsaturated cyclic hydrocarbon-based group including from 5 to 8 carbon atoms and/or polyorganosiloxanes including at least one alkylhydrogenosiloxane unit of formula:

where R is a monovalent, linear or cyclic hydrocarbon-based group including from 1 to 30 carbon atoms or a phenyl group and p is 1 or 2, and heat-crosslinkable or electro-crosslinkable thermoplastic polymers.

The crosslinking of the matrix may be chemical crosslinking, for example using succinimides as described in patent application WO 2007/082061 A2. For photo-crosslinkable matrices requiring a photoinitiator, the photoinitiator is chosen, for example, from the following list: DMPA (dimethoxy 2-phenylacetophenone), 2-benzyl-2-(dimethylamino)-1-[4-(4-morpholinophenyl]-1-butanone sold under the brand name Irgacure® 369 by Ciba®, 4,4'-bis(diethylamino)benzophenone sold by Sigma-Aldrich®, 2-hydroxy-4'-(2-hydroxyethoxy)-2-methylpropiophenone sold by Sigma-Aldrich®, 2-benzyl-2-(dimethylamino)-4'-morpholinobutyrophenone sold by Sigma-Aldrich®, phenylbis (2,4,6-trimethylbenzoyl)phosphine oxide sold by Sigma-Aldrich®, isopropylthioxanthone sold by Sigma-Aldrich®, and camphorolactone.

The PEG diacrylates can crosslink, for example, with the aid of a photoinitiator such as camphorolactone.

Among inorganic matrices, examples that may be mentioned include metal oxide matrices, especially made of $SiO_2$, $TiO_2$ or $ZrO$, or $CaCO_3$ or Si matrices.

According to preferred embodiments of the present invention, the opals are direct opals, the nanoparticles of which are constituted of filled particles made of inorganic material such as $SiO_2$, $TiO_2$ or $ZnO$, or of composite material corresponding to a mixture thereof.

According to particularly preferred embodiments of the present invention, the opals are direct opals, the nanoparticles of which are constituted of filled $SiO_2$ particles.

By way of example, mention may be made of direct opals made from the aqueous dispersion of silica particles (Cosmo S-160NP from JGC). The opals are obtained by spray-drying according to the following preparation method.

The commercial dispersion is used as obtained, or is mixed with water to obtain a mass concentration of particles equal to 18%.

The dispersion thus obtained is introduced into an atomizer (Niro Minor Production), the injection rate being set at 3800 g/h, the turbine speed being set at 37 800 rpm and the atomization temperature being set at 290° C.

The mass content of photonic particles is preferably from 0.1% to 50% and preferentially from 0.5% to 15% by weight, relative to the total weight of the composition.

Acrylic Polymer c)

According to the invention, the polymer c) according to the invention comprises monomeric units of formulae (A) and (B):

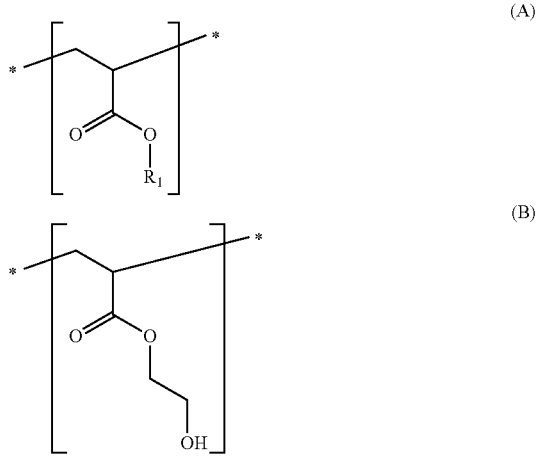

in which:

R1, independently at each instance, is chosen from alkyl and alkylene radicals, and at least 60% by weight of the groups R1 are radicals chosen from stearyl and behenyl radicals, the weight percentage relating to the sum of all the groups R1 present in the polymer, and the weight ratio of the sum of all the hydroxyethyl acrylate units to the sum of all the acrylate units bearing the group R1 ranges from 1:30 to 1:1, and the sum of the total of units A and B is at least 95% by weight of the total weight of the polymer.

Preferably, R1 consists of alkyl radicals, preferably of C16-C22 alkyl radicals, and more preferentially stearyl (C18) radicals or of behenyl (C22) radicals.

Preferably, at least 70% by weight of the groups R1 are stearyl or behenyl radicals, preferentially at least 80% by weight and more preferentially at least 90% by weight.

According to one preferred embodiment, all the groups R1 are behenyl radicals.

According another preferred embodiment, all the groups R1 are stearyl radicals.

Preferably, said weight ratio ranges from 1:15 to 1:1 and preferentially ranges from 1:10 to 1:4.

Advantageously, the polymer units present in the polymer consist of the units (A) and (B) previously described.

The polymer has a number-average molecular weight $M_n$ ranging from 2000 to 9000 g/mol, preferably ranging from 5000 to 9000 g/mol. The number-average molecular weight may be measured via the gel permeation chromatography method, for example according to the method described in the example hereinbelow.

Preferably, the polymer has a melting point ranging from 40° C. to 70° C. and preferentially ranging from 45° C. to 67° C. The melting point is measured by differential scanning calorimetry (DSC), for example according to the method described in the example hereinbelow.

According to a first embodiment, when the polymer is such that at least 60% by weight of the groups R1 are stearyl radicals, then the polymer preferably has a melting point ranging from 40 to 60° C., and preferentially ranging from 45 to 55° C.

According to a second embodiment, when the polymer is such that at least 60% by weight of the groups R1 are behenyl radicals, then the polymer has a melting point ranging from 60° C. to 70° C., and preferentially ranging from 63° C. to 67° C.

The polymer used according to the invention may be prepared by polymerization of a monomer of formula CH2=CH—COO—R1, R1 having the meaning previously described, and of 2-hydroxyethyl acrylate.

The polymerization may be performed according to known methods, such as solution polymerization or emulsion polymerization.

The polymerization is, for example, described in US 2007/0264204.

The polymer(s) c) according to the invention are preferably present in the composition in accordance with the invention in an amount ranging from 0.01% to 15% by weight, especially from 0.05% to 8% by weight and in particular from 0.1% to 5% by weight relative to the total weight of the composition.

UV-Screening Agents

The composition in accordance with the invention also comprises at least one UV-screening agent (agent for screening out UV radiation from sunlight). The UV-screening agent(s) may be chosen from hydrophilic, lipophilic or insoluble organic UV-screening agents and inorganic UV-screening agents, and mixtures thereof.

The term "UV-screening agent" means a substance that is capable of absorbing at least a portion of the UV radiation emitted by the sun, to protect the skin and/or the lips and/or the hair against the harmful effects of this radiation.

The UV-screening agent is a UV-screening agent normally used in cosmetics. It may be chosen from the positive list contained in Annex VI of (EC) Regulation No. 1223/2009, which specifies the list of UV-screening agents permitted in cosmetics.

According to a particular embodiment, the UV-screening agent(s) are present in the compositions according to the invention in an active material content ranging from 0.1% to 60% by weight and in particular from 5% to 45% by weight, relative to the total weight of the composition.

The water-soluble organic UV-screening agents are especially chosen from the following families:

Water-soluble screening agents capable of absorbing UV rays from 320 to 400 nm (UVA)

Terephthalylidenedicamphorsulfonic acid manufactured under the name Mexoryl SX by Chimex, Bis-benzazolyl derivatives as described in patents EP 669 323 and U.S. Pat. No. 2,463,264, and more particularly the compound disodium phenyldibenzimidazole tetrasulfonate sold under the trade name Neo Heliopan AP by Haarmann & Reimer, The preferred screening agent is terephthalylidenedicamphorsulfonic acid.

Water-soluble screening agents capable of absorbing UV rays from 280 to 320 nm (UVB)

p-Aminobenzoic acid (PABA) derivatives
PABA,
Glyceryl PABA and
PEG-25 PABA sold under the name Uvinul P25 by BASF,
Phenylbenzimidazole sulfonic acid sold especially under the trade name Eusolex 232 by Merck,
Ferulic acid,
Salicylic acid,
DEA methoxycinnamate,
Benzylidenecamphorsulfonic acid manufactured under the name Mexoryl SL by Chimex,
Camphorbenzalkonium methosulfate manufactured under the name Mexoryl SO by Chimex, and.

The preferred screening agent is phenylbenzimidazole sulfonic acid.

Mixed UVA and UVB water-soluble screening agents
Benzophenone derivatives including at least one sulfonic radical
Benzophenone-4, sold under the trade name Uvinul MS40 by BASF,
Benzophenone-5, and
Benzophenone-9.

When the absorber is an organic UV-screening agent of sulfonic acid type, it is preferably combined with an amount of an organic base, such as an alkanolamine, so as to make it water-soluble.

The term "alkanolamine" means a $C_2$-$C_{10}$ compound comprising at least one primary, secondary or tertiary amine function and at least one alcohol, generally primary alcohol, function.

As suitable alkanolamines, mention may be made of tromethanine and triethanolamine.

The organic screening agents, which are hydrophobic or insoluble in the usual solvents, may be chosen especially from various families of chemical compounds.

Hydrophobic Screening Agents Capable of Absorbing UV Rays from 320 to 400 nm (UVA)

Dibenzoylmethane Derivatives
Butylmethoxydibenzoylmethane sold especially under the trade name Parsol 1789 by DSM Nutritional Products, Inc.,
Isopropyldibenzoylmethane.
Aminobenzophenones
n-Hexyl 2-(4-diethylamino-2-hydroxybenzoyl)benzoate, sold under the trade name Uvinul A+ by BASF.
Anthranilic Derivatives
Menthyl anthranilate sold under the trade name Neo Heliopan MA by Symrise.
4,4-Diarylbutadiene Derivatives
1,1-Dicarboxy(2,2'-dimethylpropyl)-4,4-diphenylbutadiene, The preferential screening agents are butylmethoxydibenzoylmethane and n-hexyl 2-(4-diethylamino-2-hydroxybenzoyl)benzoate.

Hydrophobic Screening Agents Capable of Absorbing UV Rays from 280 to 320 nm (UVB)
para-Aminobenzoates
Ethyl PABA,
Ethyl dihydroxypropyl PABA,
Ethylhexyl dimethyl PABA (Escalol 507 from ISP).

Salicylic Derivatives
Homosalate sold under the name Eusolex HMS by Rona/EM Industries,
Ethylhexyl salicylate sold under the name Neo Heliopan OS by Symrise,
Dipropylene glycol salicylate sold under the name Dipsal by Scher,
TEA salicylate sold under the name Neo Heliopan TS by Symrise.
Cinnamates
Ethylhexyl methoxycinnamate sold especially under the trade name Parsol MCX by DSM Nutritional Products, Inc.,
Isopropyl methoxycinnamate,
Isoamyl methoxycinnamate sold under the trade name Neo Heliopan E 1000 by Symrise,
Diisopropyl methylcinnamate,
Cinoxate,
Glyceryl ethylhexanoate dimethoxycinnamate.)
β,β'-Diphenylacrylate Derivatives
Octocrylene sold especially under the trade name Uvinul N539 by BASF,
Etocrylene sold in particular under the trade name Uvinul N35 by BASF.
Benzylidenecamphor Derivatives
3-Benzylidenecamphor manufactured under the name Mexoryl SD by Chimex,
Methylbenzylidenecamphor sold under the name Eusolex 6300 by Merck,
Polyacrylamidomethylbenzylidenecamphor manufactured under the name Mexoryl SW by Chimex.
Triazine Derivatives
Ethylhexyltriazone sold especially under the trade name Uvinul T150 by BASF,
Diethylhexyl butamido triazone, sold under the trade name Uvasorb HEB by Sigma 3V,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
2,4-Bis(n-butyl 4'-aminobenzoate)-6-(aminopropyltrisiloxane)-s-triazine,
the symmetrical triazine screening agents described in U.S. Pat. No. 6,225,467, patent application WO 2004/085412 (see compounds 6 and 9) or the document "Symmetrical Triazine Derivatives" IP.COM Journal, IP.COM Inc West Henrietta, NY, USA (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine, which is also mentioned in the Beiersdorf patent applications WO 06/035000, WO 06/034982, WO 06/034991, WO 06/035007, WO 2006/034992 and WO 2006/034985.
Imidazoline Derivatives
Ethylhexyl dimethoxybenzylidene dioxoimidazo line propionate.
Benzalmalonate Derivatives
Polyorganosiloxanes containing benzalmalonate functions, for instance Polysilicone-15, sold under the trade name Parsol SLX by DSM Nutritional Products, Inc.,
Dineopentyl 4'-methoxybenzalmalonate.
Merocyanine Derivatives
Octyl 5-N,N-diethylamino-2-phenylsulfonyl-2,4-pentadienoate, The preferred screening agents are homosalate, ethylhexylsalicylate, octocrylene, ethylhexyl, methoxycinnamate, isoamyl methoxycinnamate, ethylhexyl triazone and diethylhexyl butamido triazone.

The most preferential are ethylhexyl salicylate, octocrylene, ethylhexyl triazone, and ethylhexyl methoxycinnamate.

Mixed Hydrophobic Screening Agents Capable of Absorbing Both UVA and UVB Rays

Benzophenone Derivatives

Benzophenone-1 sold under the trade name Uvinul 400 by BASF,

Benzophenone-2 sold under the trade name Uvinul D50 by BASF,

Benzophenone-3 or oxybenzone sold under the trade name Uvinul M40 by BASF,

Benzophenone-5,

Benzophenone-6 sold under the trade name Helisorb 11 by Norquay,

Benzophenone-8 sold under the trade name Spectra-Sorb UV-24 by American

Cyanamid,

Benzophenone-10,

Benzophenone-11,

Benzophenone-12.

Phenylbenzotriazole Derivatives

Drometrizole trisiloxane sold under the name Silatrizole by Rhodia Chimie, Methylenebis(benzotriazolyl)tetramethylbutylphenol sold in solid form under the trade name MIXXIM BB/100 by Fairmount Chemical, or in micronized form as an aqueous dispersion under the trade name Tinosorb M by Ciba Specialty Chemicals.

Bis-Resorcinyl Triazine Derivatives

Bis(ethylhexyloxyphenol)methoxyphenyltriazine sold under the trade name Tinosorb S by Ciba Geigy.

Benzoxazole Derivatives 2,4-Bis[5-1(dimethylpropyl)benzoxazol-2-yl-(4-phenyl)imino]-6-(2-ethylhexyl)imino-1,3,5-triazine, sold under the name Uvasorb K2A by Sigma 3V.

The preferential screening agents are:

Drometrizole trisiloxane,

Methylenebis(benzotriazolyl)tetramethylbutylphenol,

Bis(ethylhexyloxyphenol) methoxyphenyltriazine, and

Benzophenone-3 or Oxybenzone.

The most preferential screening agents are:

Drometrizole trisiloxane, and

Bis(ethylhexyloxyphenol)methoxyphenyltriazine.

Mention may also be made of merocyanine-type screening agents such as those prepared according to the protocols described in WO 2007/071582, in IP.com Journal (2009), 9(5A), 29-30 IPCOM000182396D under the title "Process for producing 3-amino-2-cyclohexan-1-ylidene compounds" and in U.S. Pat. No. 4,749,643 (column 13, line 66-column 14, line 57 and the references cited in this regard).

Inorganic Sunscreens or Photoprotective Agents

The inorganic photoprotective agents are chosen from coated or uncoated metal oxide pigments (mean size of the primary particles: generally between 5 nm and 100 nm, preferably between 10 nm and 50 nm), for instance titanium oxide (amorphous or crystallized in rutile and/or anatase form), iron oxide, zinc oxide, zirconium oxide or cerium oxide pigments, which are all UV-photoprotective agents that are well known per se.

The pigments may or may not be coated.

The coated pigments are pigments that have undergone one or more surface treatments of chemical, electronic, mechanochemical and/or mechanical nature with compounds as described, for example, in Cosmetics & Toiletries, February 1990, Vol. 105, pages 53-64, such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

As is known, silicones are organosilicon polymers or oligomers comprising a linear or cyclic and branched or crosslinked structure, of variable molecular weight, obtained by polymerization and/or polycondensation of suitably functionalized silanes and essentially constituted of a repetition of main units in which the silicon atoms are connected to each other via oxygen atoms (siloxane bond), optionally substituted hydrocarbon-based radicals being connected directly to said silicon atoms via a carbon atom.

The term "silicones" also encompasses the silanes required for their preparation, in particular alkylsilanes.

The silicones used for coating the pigments that are suitable for the present invention are preferably chosen from the group containing alkylsilanes, polydialkylsiloxanes and polyalkylhydrosiloxanes. Even more preferentially, the silicones are chosen from the group containing octyltrimethylsilane, polydimethylsiloxanes and polymethylhydrosiloxanes.

Needless to say, before being treated with silicones, the metal oxide pigments may have been treated with other surface agents, in particular with cerium oxide, alumina, silica, aluminium compounds or silicon compounds, or mixtures thereof.

The coated pigments are more particularly titanium oxides that have been coated:

with silica, such as the product Sunveil from the company Ikeda, with silica and iron oxide, such as the product Sunveil F from from the company Ikeda, with silica and alumina, such as the products Microtitanium Dioxide MT 500 SA and Microtitanium Dioxide MT 100 SA from the company Tayca and Tioveil from the company Tioxide, with alumina, such as the products Tipaque TTO-55 (B) and Tipaque TTO-55 (A) from the company Ishihara and UVT 14/4 from the company Kemira, with alumina and aluminium stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR 351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca, $TiO_2$ treated with octyltrimethylsilane, sold under the trade name T 805 by the company Degussa Silices, $TiO_2$ treated with a polydimethylsiloxane, sold under the trade name 70250 Cardre UF TiO2SI3 by the company Cardre, and anatase/rutile $TiO_2$ treated with a polydimethylhydrogenosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackher under the name Transparent titanium oxide PW, by the company Miyoshi Kasei under the name UFTR, by the company Tomen under the name ITS and by the company Tioxide under the name Tioveil AQ.

The uncoated zinc oxide pigments are, for example:

those sold under the name Z-Cote by the company Sunsmart, those sold under the name Nanox by the company Elementis, those sold under the name Nanogard WCD 2025 by the company Nanophase Technologies.

The coated zinc oxide pigments are, for example:

those sold under the name Zinc Oxide CS-5 by the company Toshibi (ZnO coated with polymethylhydrosiloxane), those sold under the name Nanogard Zinc Oxide FN by the company Nanophase Technologies (as a 40% dispersion in Finsolv TN, $C_{12}$-$C_{15}$ alkyl benzoate), those sold under the name Daitopersion ZN-30 and Daitopersion ZN-50 by the company Daito (dispersions in cyclopolymethylsiloxane/oxyethylenated polydimethylsiloxane, containing 30% or 50% of nano zinc oxides coated with silica and polymethylhydrosiloxane), those sold under the name NFD Ultrafine ZnO by the company Daikin (ZnO coated with perfluoroalkyl phosphate and copolymer based on perfluoroalkylethyl as a dispersion in cyclopentasiloxane), those sold under the name SPD-Z1 by the company Shin-Etsu (ZnO coated with silicone-grafted acrylic polymer, dispersed in cyclodimethylsiloxane), those sold under the name Escalol Z100 by the company ISP (alumina-treated ZnO dispersed in an ethylhexyl methoxycinnamate/PVP-hexadecene/methicone copolymer mixture), those sold under the name Fuji ZnO-SMS-10 by the company Fuji Pigment (ZnO coated with silica and polymethylsilsesquioxane), those sold under the name Nanox Gel TN by the company Elementis (ZnO dispersed at a concentration of 55% in $C_{12}$-$C_{15}$ alkyl benzoate with hydroxystearic acid polycondensate).

The uncoated cerium oxide pigments are sold under the name Colloidal Cerium Oxide by the company Rhone-Poulenc.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

These metal oxide particles taken per se do not constitute photonic particles as defined according to the invention.

The inorganic screening agent(s) may be present in the compositions according to the invention in a concentration of between 0.1% and 15% and preferably between 0.2% and 10% by weight relative to the total weight of the composition.

Preferably, the mass ratio of the photonic particles to the polymer c) is from 0.1 to 20, preferably from 0.5 to 10.

The compositions according to the invention comprise at least one aqueous phase.

An aqueous phase contains water and optionally other water-soluble or water-miscible organic solvents.

An aqueous phase that is suitable for use in the invention may comprise, for example, a water chosen from a natural spring water, such as water from La Roche-Posay, water from Lucas, water from Vittel, water from Saint-Gervais or waters from Vichy, or a floral water.

The composition according to the invention may also contain at least one polar organic solvent, which is preferably physiologically acceptable.

The polar organic solvents are generally water-miscible.

As polar organic solvent, mention may be made of $C_1$-$C_6$ monoalcohols such as ethanol or isopropanol; $C_1$-$C_6$ polyols such as glycerol, 1,3-propanediol, 1,4-butanediol, 1,5-pentanediol and 1,6-hexanediol; $C_1$-$C_6$ alkylene glycols such as ethylene glycol, propylene glycol, dipropylene glycol, butylene glycol, pentylene glycol and hexylene glycol; and mixtures thereof.

The total content of $C_1$-$C_6$ alcohols in the composition of the invention is preferably from 0.1% to 10% by weight and preferentially from 1% to 5% by weight of $C_1$-$C_6$ alcohols relative to the total weight of the composition.

The total content of $C_1$-$C_6$ alkylene glycols in the composition of the invention is preferably from 0.1% to 30% by weight and preferentially from 5% to 25% by weight of $C_1$-$C_6$ alkylene glycols relative to the total weight of the composition.

The composition according to the invention may include a volatile solvent.

For the purposes of the invention, the term "volatile solvent" means any liquid that is capable of evaporating on contact with keratin materials, at room temperature and atmospheric pressure.

The composition according to the invention may be chosen especially so that the composition contains at least 5%, or even at least 30%, or even at least 40% of volatile solvent.

Fatty Phase

The composition according to the invention may include a fatty phase. The fatty phase may especially be volatile.

The composition may include an oil, for instance synthetic esters and ethers, linear or branched hydrocarbons of mineral or synthetic origin, fatty alcohols containing from 8 to 26 carbon atoms, partially hydrocarbon-based and/or silicone-based fluoro oils, silicone oils such as volatile or non-volatile polymethylsiloxanes (PDMS) bearing a linear or cyclic silicone chain, which are liquid or pasty at room temperature, and mixtures thereof, other examples being given hereinbelow.

A composition in accordance with the invention may thus comprise at least one volatile oil.

Volatile Oils

For the purposes of the present invention, the term "volatile oil" means an oil (or non-aqueous medium) that is capable of evaporating on contact with the skin in less than one hour, at room temperature and at atmospheric pressure.

The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferably ranging from 1.3 Pa to 1300 Pa (0.01 to 10 mmHg).

The volatile hydrocarbon-based oils may be chosen from hydrocarbon-based oils of animal or plant origin containing from 8 to 16 carbon atoms, and especially branched $C_8$-$C_{16}$ alkanes (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, especially those with a viscosity 8 centistokes ($8 \times 10^{-6}$ m2/s), and especially containing from 2 to 10 silicon atoms and in particular from 2 to 7 silicon atoms, these silicones optionally including alkyl or alkoxy groups containing from 1 to 10 carbon atoms. As volatile silicone oil that may be used in the invention, mention may be made especially of dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Volatile fluoro oils such as nonafluoromethoxybutane or perfluoromethylcyclopentane, and mixtures thereof, may also be used.

It is also possible to use a mixture of the oils mentioned above.

Non-Volatile Oils

A composition according to the invention may include a non-volatile oil.

For the purposes of the present invention, the term "non-volatile oil" means an oil with a vapour pressure of less than 0.13 Pa and especially oils of high molar mass.

The non-volatile oils may be chosen especially from non-volatile hydrocarbon-based oils, which may be fluorinated, and/or silicone oils.

As non-volatile hydrocarbon-based oil that may be suitable for use in the invention, mention may be made especially of:

hydrocarbon-based oils of animal origin, hydrocarbon-based oils of plant origin such as phytostearyl esters, such as phytostearyl oleate, phytostearyl isostearate and lauroyl/octyldodecyl/phytostearyl glutamate, for example sold under the name Eldew PS203 by Ajinomoto, triglycerides constituted of fatty acid esters of glycerol, the fatty acids of which may have chain lengths ranging from $C_4$ to $C_{24}$, these chains possibly being linear or branched, and saturated or unsaturated; these oils are especially heptanoic or octanoic triglycerides, wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cotton seed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passion flower oil or musk rose oil; shea butter; or alternatively caprylic/capric acid triglycerides, for instance those sold by the company Stéarinerie Dubois or those sold under the names Miglyol 810®, 812® and 818® by the company Dynamit Nobel, hydrocarbon-based oils of mineral or synthetic origin, for instance:

synthetic ethers containing from 10 to 40 carbon atoms, linear or branched hydrocarbons of mineral or synthetic origin, such as petroleum jelly, polydecenes, hydrogenated polyisobutene such as Parleam, and squalane, and mixtures thereof, and in particular hydrogenated polyisobutene, synthetic esters, such as the oils of formula $R_1COOR_2$, in which $R_1$ represents a linear or branched fatty acid residue including from 1 to 40 carbon atoms and R2 represents an especially branched hydrocarbon-based chain containing from 1 to 40 carbon atoms, with the proviso that $R_1+R_2$ is ≥10.

The esters may be chosen especially from especially fatty acid esters, for instance:

cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate, polyol esters and pentaerythrityl esters, for instance dipentaerythrityl tetrahydroxystearate/tetraisostearate, esters of diol dimers and of diacid dimers, such as Lusplan DD-DA5® and Lusplan DD-DA7® sold by the company Nippon Fine Chemical and described in patent application FR 0302809, fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol, higher fatty acids such as oleic acid, linoleic acid and linolenic acid, and mixtures thereof; and dialkyl carbonates, the two alkyl chains possibly being identical or different, such as the dicaprylyl carbonate sold under the name Cetiol CC® by Cognis, non-volatile silicone oils, for instance non-volatile polydimethylsiloxanes (PDMSs), polydimethylsiloxanes comprising alkyl or alkoxy groups that are on the side and/or at the end of a silicone chain, these groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and dimethicones or phenyl trimethicones with a viscosity of less than or equal to 100 cSt, and mixtures thereof, and mixtures thereof.

The composition containing the photonic particles may be free of oil, and in particular may contain no non-volatile oil.

Additives

The composition including the photonic particles may comprise at least one additive chosen from adjuvants that are common in the cosmetic field, such as fillers, colouring agents, hydrophilic or lipophilic gelling agents, water-soluble or liposoluble active agents, preserving agents, moisturizers such as polyols and especially glycerol, sequestrants, antioxidants, solvents, fragrances, odour absorbers, pH adjusters (acids or bases) and mixtures thereof.

The composition may contain at least one active agent which has a supplementary activity in the field of solar protection, such as antioxidants, bleaching agents in the context of anti-pigmentation and depigmentation, and anti-ageing active agents.

The additive(s) may be chosen from those mentioned in the CTFA Cosmetic Ingredient Handbook, 10'h Edition Cosmetic and Fragrance Assn, Inc., Washington DC (2004), incorporated herein by reference.

Presentation Forms

The composition according to the invention may be a lotion, a two-phase composition, a cream, a milk, an ointment or a gel, for the skin, the lips, the hair or the nails.

Photoprotective Cosmetic Composition

According to another of its aspects, the invention relates to a photoprotective cosmetic composition comprising, in a physiologically acceptable medium, a composition according to the invention as defined above.

The term "physiologically acceptable medium" means a non-toxic medium that may be applied to human keratin materials, in particular the skin, mucous membranes or the integuments.

This medium is adapted to the nature of the support onto which the composition is to be applied, and also to the form in which the composition is intended to be packaged.

The composition may be packaged in any packaging device, in particular made of thermoplastic, or on any support intended for this purpose.

The packaging device may be a bottle, a pump-action bottle, an aerosol flask, a tube, a sachet or a jar.

Cosmetic Non-Therapeutic Photoprotection Process

The photoprotective cosmetic composition may be applied by hand or using an applicator.

The application may also be performed by spraying or projection using, for example, a piezoelectric or aerograph device or by transfer of a layer of composition previously deposited on an intermediate support.

EXAMPLES

Example 1—Preparation of Photonic Particles in Accordance with the Invention

The aqueous dispersion of silica particles (Cosmo S-160NP from JGC) was atomized according to the following process.

The commercial dispersion is used as obtained, or is mixed with water to obtain a mass concentration of particles equal to about 18%.

The dispersion thus obtained was introduced into an atomizer (Niro Minor Production), the injection rate being set at 3800 g/h, the turbine speed being set at 37 800 rpm and the atomization temperature being set at 290° C.

The opals obtained are direct opals with a mean size (D 0.5) of 12.2 μm, in the form of a dry powder.

Example 2 of Preparation of Polymer 1

Determination of the molecular weight by gel permeation chromatography (GPC):

The sample is prepared by preparing a solution of the polymer at 10 mg/ml in tetrahydrofuran. The sample is placed in an oven at 54° C. for 10 minutes and then in an oscillating shaker for 60 minutes to aid dissolution. After visual inspection, the sample appears to be totally dissolved in the solvent.

The sample prepared was analysed using two polypore 300×7.5 mm columns (manufactured by Agilent Technologies), a Waters 2695 chromatographic system, a tetrahydrofuran mobile phase and detection by refractive index. The sample was filtered through a 0.45 μm nylon filter, before being injected into the liquid chromatograph. The standards used for the calibration are the Easi Vial narrow polystyrene (PS) standards from Agilent Technologies.

Polystyrene standards ranging from 2 520 000 to 162 daltons were used for the calibration.

The system is equipped with a PSS SECcurity 1260 RI detector. The polystyrene calibration curve was used to determine the average molecular weight. The recording of the diagrams and the determination of the various molecular weights were performed by the Win GPC Unichrom 81 program.

Determination of the melting point by differential scanning calorimetry (or DSC):

This method describes the general procedure for determining the melting point of polymers by differential scanning calorimetry. This method is based on the standards ASTM E791 and ASTM D 34182 and the DSC calibration is performed according to standard ASTM E 9672.

Behenyl Acrylate/2-Hydroxyethyl Acrylate Copolymer (Polymer 1):

In a 4-necked flask equipped with side-blade mixer, an internal thermometer, two funnels, a reflux condenser, and an extension for two other necks, 175 g of behenyl acrylate, 25 g of 2-hydroxyethyl acrylate and 0.4 g of 2,2'-azobis(2- methylbutyronitrile) (Akzo Nobel) were added, over the course of 60 minutes at 80° C., to 40 g of isopropanol, with stirring, after having removed the oxygen from the system by means of a nitrogen flush for 20 minutes. The mixture was stirred at 80° C. for 3 hours. The solvent was then removed by vacuum distillation, 1 g of dilauryl peroxide was then added and the reaction was continued for 60 minutes at 110° C. The step was repeated. The mixture was then cooled to 90° C., a stream of demineralized water was added and the mixture was then stirred. The water was removed by vacuum distillation.

Molecular weight: Mn=7300 g/mol, Mw=21 000, Mw/Mn=2.8

Melting point: 65° C.

Example 3 of Preparation of Polymer 2

Stearyl Acrylate/2-Hydroxyethyl Acrylate Copolymer (Polymer 2)

In a 4-necked flask equipped with side-blade mixer, an internal thermometer, two funnels, a reflux condenser, and an extension for two other necks, 155 g of behenyl acrylate, 45 g of 2-hydroxyethyl acrylate and 0.4 g of 2,2'-azobis(2-methylbutyronitrile) (Akzo Nobel) were added, over the course of 90 minutes at 80° C., to 50 g of isopropanol, with stirring, after having removed the oxygen from the system by means of a nitrogen flush for 20 minutes. The mixture was stirred at 80° C. for 3 hours. The solvent was then removed by vacuum distillation, 1 g of dilauryl peroxide was then added and the reaction was continued for 60 minutes at 125° C. The step was repeated. The mixture was then cooled to 90° C., a stream of demineralized water was added and the mixture was then stirred. The water was removed by vacuum distillation.

Molecular weight: Mn=7500 g/mol, Mw=19 000, Mw/Mn=2.6

Melting point: 49° C.

Examples 4 to 6—Preparation of a Composition in Accordance with the Invention

The following O/W emulsions were prepared:

| Phase | INCI name | 4 (invention) | 5 | 6 |
|---|---|---|---|---|
| A | Bis(ethylhexyloxyphenol) methoxyphenyltriazine | 3.00 | 3.00 | 3.00 |
| | Drometrizole trisiloxane (Mexoryl XL) | 2.00 | 2.00 | 2.00 |
| | Homosalate | 8.00 | 8.00 | 8.00 |
| | Octyl salicylate | 5.00 | 5.00 | 5.00 |
| | Diethylamino hydroxybenzoyl hexyl benzoate | 3.00 | 3.00 | 3.00 |
| | Octocrylene | 1.50 | 1.50 | 1.50 |
| | Dicaprylyl carbonate | 3.00 | 3.00 | 3.00 |
| | Diisopropyl sebacate | 3.00 | 3.00 | 3.00 |
| | Isohexadecane | 2.00 | 2.00 | 2.00 |
| | Isopropyl lauryl sarcosinate | 4.00 | 4.00 | 4.00 |
| | Poly C10-30 alkyl acrylate (Intelimer IPA-13.1) (polymer not in accordance with the invention) | | 2.00 | |
| | Behenyl alcohol (and) glyceryl stearate (and) disodium ethylene dicocamide PEG-15 disulfate (and) glyceryl stearate citrate (Ceralution H from Sasol) | 2.00 | 2.00 | 2.00 |
| | Polymer 1 according to Example 2 | 2.00 | | |

| Phase | INCI name | 4 (invention) | 5 | 6 |
|---|---|---|---|---|
| B | Glycerol | 5.00 | 5.00 | 5.00 |
| | Caprylyl glycol | 0.50 | 0.50 | 0.50 |
| | Phenylbenzimidazolesulfonic acid | 2.00 | 2.00 | 2.00 |
| | Trometharnine | 1.80 | 1.80 | 1.80 |
| | Xanthan gum | 0.50 | 0.50 | 0.50 |
| | Water | qs 100 | qs 100 | qs 100 |
| C | Photonic compound according to Example 1 | 4.00 | 4.00 | 4.00 |
| D | Denatured alcohol | 5.00 | 5.00 | 5.00 |
| | in vitro SPF | 61.1 ± 4.1 | 37.4 ± 2.5 | 31.7 ± 1.2 |
| | Transparency on the skin (Score from an expert sensory panel, out of 15: 1 = white/opaque; 15 = transparent) | 10.8 ± 2.8 | 10.8 ± 2.7 | 11.1 ± 2.1 |
| | Softness on application (Score from an expert sensory panel, out of 15: 1 = not very soft; 15 = soft) | 13.0 ± 1.1 | 13.7 ± 0.4 | 13.8 ± 0.7 |

Preparation Method

The compositions described in Examples 2 to 4 below were prepared according to the following procedure:

1—Prepare the oily phase (Phase A) by introducing the screening agents.

Dissolve the screening agents by heating to 70° C., add the fatty-phase structuring polymer and heat until the polymer has completely dissolved.

2—Prepare the aqueous phase (Phase B) and heat the phase to 70° C.

3—Emulsify the two phases together using a rotor/stator mixer such as a Moritz blender at 70° C., then cool to 30° C.

4—Introduce the photonic particles (Phase C) with slow stirring using a Rayneri blender.

5—Add phase D with slow stirring using a Rayneri blender.

Compositions 4 to 6 are homogeneous and stable for 2 months at 4° C., at room temperature and at 45° C.

The addition of polymer c) according to the invention makes it possible to increase the SPF very significantly, in contrast with another acrylic polymer not in accordance with the invention.

Composition 4 has a high SPF while at the same time having excellent cosmetic properties. The transparency on the skin and the softness are markedly superior for composition 4 according to the invention.

Results of the same type will be obtained by replacing polymer 1 with polymer 2 in composition 4.

The invention claimed is:

1. A composition comprising at least:

a) photonic particles having a mean size of from 0.5 μm to 100 μm, each including an ordered periodic arrangement of monodisperse nanoparticles or of empty spaces, leading to attenuation of the radiation in the wavelength range extending from 250 nm to 1800 nm, wherein the mass content of the photonic particles is from 0.1% to 50% by weight relative to the total weight of the composition, b) 0.01% to 60% by weight, relative to the total weight of the composition of at least one UV-screening agent, and c) from 0.01% to 15% by weight, relative to the total weight of the composition of at least one polymer comprising monomer units of formulae (A) and (B):

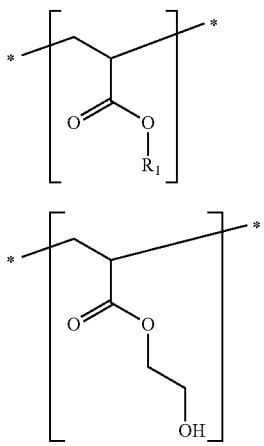

in which:

R1, independently at each instance, is chosen from alkyl and alkylene radicals,
and
at least 60% by weight of the groups R1 are radicals chosen from stearyl and behenyl radicals,
the weight percentage relating to the sum of all the groups R1 present in the polymer,
and
the weight ratio of the sum of all the hydroxyethyl acrylate units to the sum of all the acrylate units bearing the group R1 ranges from 1:30 to 1:1,
and the sum of the total of units A and B is at least 95% by weight relative to the total weight of the polymer,
the polymer having a number-average molecular weight Mn ranging from 2000 to 9000 g/mol; and wherein the composition is an emulsion.

2. The composition according to claim 1, in which the photonic particles include nanoparticles aggregated without a matrix.

3. The composition according to claim 1, in which the nanoparticles comprise silica, at least one metal oxide, or a mixture of silica and at least one metal oxide.

4. The composition according to claim 1, in which the nanoparticles are constituted of silica.

5. The composition according to claim 1, in which the mean size of the nanoparticles is from 100 nm to 500 nm.

6. The composition according to claim 1, in which the photonic particles are substantially spherical in shape.

7. The composition according to claim 1, in which the photonic particles have a mean size of from 1 μm to 40 μm.

8. The composition according to claim 1, in which the mass content of photonic particles is from 0.5% to 15% by weight relative to the total weight of the composition.

9. The composition according to claim 1, in which the at least one UV-screening agent is chosen from UV-screening agents that may be chosen from hydrophilic, lipophilic or insoluble organic UV-screening agents and inorganic UV-screening agents, and mixtures thereof.

10. The composition according to claim 1, in which the content of at least one UV-screening agent is from 5% to 45% by weight, relative to the total weight of said composition.

11. The composition according to claim 1, wherein, in polymer c), R1 consists of an alkyl radical.

12. The composition according to claim 1, wherein, in polymer c), at least 70% by weight of the groups R1 are behenyl or stearyl radicals.

13. The composition according to claim 1, wherein, in polymer c), all the groups R1 are stearyl or behenyl radicals.

14. The composition according to claim 1, wherein, in polymer c), said weight ratio ranges from 1:15 to 1:1.

15. The composition according to claim 1, wherein polymer c) has a number-average molecular weight Mn ranging from 5000 to 9000 g/mol.

16. The composition according to claim 1, wherein polymer c) has a melting point ranging from 40° C. to 70° C.

17. The composition according to claim 1, wherein, in polymer c), at least 60% by weight of the groups R1 are stearyl radicals, and polymer c) has a melting point ranging from 40 to 60° C.

18. The composition according to claim 1, wherein, in polymer c), at least 60% by weight of the groups R1 are behenyl radicals, and said polymer c) has a melting point ranging from 60° C. to 70° C.

19. The composition according to claim 1, wherein the content of polymer c) is from 0.05% to 8% by weight, relative to the total weight of said composition.

20. The composition according to claim 1, being a cosmetic composition in the form of an oil in water emulsion and having a SPF value of at least 30, and wherein the mass content of the photonic particles is from 0.5% to 15% by weight, relative to the total weight of the composition; the content of the at least one UV-screening agent is from 5% to 45% by weight, relative to the total weight of the composition, the content of the polymer c) is from 0.05% to 8% by weight, relative to the total weight of the composition, the weight ratio of the sum of all the hydroxyethyl acrylate units to the sum of all the acrylate units bearing the group R1 ranges from 1:10 to 1:4 and the mass ratio of the photonic particles to the polymer c) is from 0.1 to 20.

21. The composition according to claim 1, being a cosmetic composition in the form of an oil in water emulsion.

22. A non-therapeutic process for the photoprotection of keratin materials with respect to solar UV radiation, comprising a step of applying a cosmetic composition according to claim 1 to said keratin materials.

* * * * *